United States Patent [19]
Caboche

[11] Patent Number: 5,989,352
[45] Date of Patent: Nov. 23, 1999

[54] LACTITOL COMPOSITION AND PROCESS FOR THE PREPARATION THEREOF

[75] Inventor: Jean-Jacques Caboche, le Marais, France

[73] Assignee: Roquette Freres, Lestrem, France

[21] Appl. No.: 08/934,649

[22] Filed: Sep. 23, 1997

[30] Foreign Application Priority Data

Sep. 27, 1996 [FR] France ................................. 96 11804

[51] Int. Cl.$^6$ ............................. C13F 1/02; A23G 3/00; A61K 47/26
[52] U.S. Cl. ............................... 127/58; 127/30; 127/31; 127/60; 127/61; 426/658; 536/1.11; 536/127; 514/53; 514/777
[58] Field of Search ................................. 127/61, 30, 31, 127/58; 514/53, 777; 536/1.11, 127; 426/658

[56] References Cited

U.S. PATENT DOCUMENTS 5,494,525  2/1996  Heikkila ..................................... 127/61

FOREIGN PATENT DOCUMENTS

| | | |
|---|---|---|
| 0 039 981 | 11/1981 | European Pat. Off. . |
| 0 381 483 | 8/1990 | European Pat. Off. . |
| 02-196794 | 8/1990 | Japan . |
| 02-200 695 | 8/1990 | Japan . |
| 02-25694 | 10/1990 | Japan . |
| 04-013686 | 1/1992 | Japan . |
| 90/06317 | 6/1990 | WIPO . |
| 92/16542 | 10/1992 | WIPO . |

OTHER PUBLICATIONS

Journal of the American Chemical Society, 1938, vol. 60 p 571–573, by Wolfrom et al.
Journal of Agriculture, Food and Chemistry, 1979, vol. 27 No. 4 p 680–686, by Velthuijsen.
6th European Meeting of Crystallography, Barcelone 1980, Bommel et al.
Comptes rendus hebdomadaires des Séances de l'Académie des Sciences, 1920, vol. 170, p 47–50, by J.B. Senderens.
Journal of the American Chemical Society, 1952, vol. 74, p 1105, by Wolfrom et al.

*Primary Examiner*—Evelyn Mei Huang
*Attorney, Agent, or Firm*—Henderson & Sturm

[57] ABSTRACT

The invention relates to a new anhydrous lactitol crystalline composition exhibiting essentially a porous and cellular structure and possessing a very high lactitol crystalline purity. This composition has remarkable functional properties, making its use particularly recommended in the manufacture of tablets or various powders to be dissolved in water. The invention also relates to a new process which makes it possible to manufacture the crystalline lactitol composition.

27 Claims, 3 Drawing Sheets

LACTITOL COMPOSITION AND PROCESS FOR THE PREPARATION THEREOF

The present invention relates to a new anhydrous crystalline composition of lactitol having very high crystalline purity and with a porous and cellular structure. It also relates to a specific process for producing this composition and to the uses of the latter in industry.

4-O-β-D-Galactopyranosyl-D-glucitol, commonly known as lactitol, is a polyol obtained industrially by hydrogenation of lactose. It is of great interest because of the fact that it is more stable chemically and less calorific than sucrose while advantageously possessing the property of being suitable for use in foods for diabetics. Moreover, lactitol possesses the distinctive feature of not being cariogenic, which offers it, and has already offered it, numerous applications in industry, in particular in the food and pharmaceutical industries.

Lactitol is generally sold in the form of a crystalline powder. Its crystallography is particularly complex when reference is made to the literature, from which it emerges that this polyol can crystallize simultaneously in various anhydrous, monohydrate, dihydrate or indeed even trihydrate forms.

With respect to the anhydrous form, Wolfrom et al. seem to have been the first to report, in 1938 in the Journal of the American Chemical Society, 60, 571–573, the existence of an anhydrous crystalline product with a melting point in the region of 146° C.

Anhydrous lactitol crystals with a markedly lower melting point, between 121° C. and 124° C., are described in Patent Application JP 2-200 695, published in 1990.

A crystalline product in the monoclinic form, with a well-defined unit cell, having a melting point of between 149° C. and 152° C., is also known. This product formed the subject of Patent Application WO 92/16542, published in 1992. This product strongly resembles that described two years previously in JP 2-255 694.

As regards lactitol crystallized in the monohydrate form, that is to say with a single water molecule, Velthuijsen reported, in 1979 in the Journal of Agriculture, Food and Chemistry, 27, 680–686, a product having a melting point of between 94° C. and 97° C. For their part, Bommel et al., during a lecture given at the 6th European Meeting of Crystallography, held in Barcelona in 1980, presented the results of their work and showed that, by crystallizing lactitol from a 50% aqueous/alcoholic solution, crystals were obtained in the orthorhombic monohydrate form with a specific crystalline unit cell and with a melting point of 102° C.

Still with respect to the monohydrate form, the company C.V. Chemie Combinate Amsterdam made public in 1981 the existence of a lactitol monohydrate exhibiting all the characteristics described by Bommel et al., apart from the fact that the melting point of the product shown is between 121° C. and 123° C. This product formed the subject of European Patent Application EP 039 981.

Finally, a product composed virtually exclusively of lactitol monohydrate having a melting point between 90° C. and 105° C. is known. This product exhibits a crystalline unit cell similar to that described by Bommel et al. and is described in Patent Application WO 90/06317, published in 1990, and in Patent Application JP 2 196 794, published in 1991.

As regards the dihydrate form, it has been known for a long time since a priori already in 1920, in a note published in the Comptes Rendus Hebdomadaires des Séances de l'Académie des Sciences, 170, 47–50, J. B. Senderens described orthorhombic lactitol crystals with a melting point in the region of 78° C. The results of Wolfrom et al., published in 1952 in the Journal of the American Chemical Society, 74, 1105, also report the existence of a lactitol dihydrate with a melting point of between 72.5° C. and 74° C. Finally, Bommel et al., during the presentation of their work at the 6th European Meeting of Crystallography in Barcelona in 1980, confirmed the existence of lactitol dihydrate crystals with a melting point in the region of 78° C. and furthermore characterized the crystalline unit cell of these crystals, both in its dimensions and its structure.

Lactitol can also crystallize in the trihydrate form, if reference is made to European Application EP 381 483, published in 1990. Such crystals have a melting point of between 52° C. and 56° C. This is confirmed in Japanese Application JP 4-13686, published in 1992.

In short, it will be accepted that lactitol can crystallize in various states of hydration and in more or less stable forms and that there generally exist, for this polyol, several crystalline forms for the same state of hydration.

It should be noted here that the number of known crystalline forms of lactitol cannot be compared with that known for other sugars or polyols. For example, to date, only a single crystalline form is known for sucrose, maltose, xylitol, erythritol or maltitol, and only two or three crystalline forms for, for example, dextrose and mannitol.

This explains why, in the case of lactitol, it has always been difficult, in contrast to the other sugars and polyols, to obtain essentially a single crystalline form uncontaminated by other forms. To date, control of the crystallization remains imperfect, as is shown in particular by the documents WO 92/16542 and JP 2-255 694 or alternatively WO 90/06317, which have been published very recently.

In International Application WO 92/16542, it is recommended, to obtain anhydrous crystals with a melting point in the region of 150° C., to crystallize from water starting with highly concentrated, supersaturated solutions constantly maintained at a high temperature. The absence of systematic addition of a crystalline initiator intended to direct the crystallization solely towards this crystalline form means that the final product can contain not insignificant amounts of crystals of hydrated form. No other method of manufacture is made known in this document for manufacturing this product.

Another method for producing anhydrous crystals with a melting point in the region of 150° C. is found in Japanese Application JP 2-255 694. According to this document, crystallization is carried out by feeding, preferably continuously, a mixer-extruder with a chemically pure lactitol syrup, concentrated to a solids content of more than 90% and maintained at a temperature greater than 80° C., and by initiating the crystallization with any lactitol crystals, so that this crystallization is rapid. It is said that it is essential to use, for the syrup intended to be crystallized, the concentration and temperature conditions quoted above, so as not to contaminate the final product with hydrated forms or another anhydrous form than that desired.

This patent application furthermore presents other methods which can be envisaged for the production of anhydrous crystals, such as crystallization in aqueous/alcoholic solution, crystallization by the so-called "masse" (compact mass) technique or alternatively atomization, but these methods are automatically excluded because they do not make it possible, according to the description, to obtain products which only contain the desired crystalline form with a melting point in the region of 150° C.

As regards Patent Application WO 90/06317, it relates to the preparation of lactitol by crystallization from water, under well-defined temperature and concentration conditions, so as to obtain only crystals in the monohydrate form with a specific melting point. No other method is presented or even suggested.

It is observed that only crystallization from water and crystallization using a mixer-extruder are known as being able to make it possible, under very specific conditions, to obtain lactitol crystallized essentially in a single crystalline form. Moreover, these techniques are today virtually the only ones to be employed industrially. The products obtained are particularly well-suited to certain applications, such as those in chewing gum or chocolate.

However, it is in other applications that these products are not entirely satisfactory. This is the case, for example, when it is desired to use lactitol to replace sucrose or lactose in dry pharmaceutical forms, such as hard gelatin capsules, medicaments of the soluble powder type, tablets and pulverulent nutrient preparations to be diluted. This is also the case when it is desired to carry out the same type of substitution in sugar-containing foods, such as powdered drinks, desserts, cake preparations or chocolate-flavoured or vanilla-flavoured breakfast powders.

It is observed in these specific applications, both for crystalline lactitol powders obtained by the kneading-extrusion technique and for crystalline lactitol powders obtained by crystallization from water, that these exhibit a number of faults, such as, in particular, those of flowing with difficulty, of being subject to solidification or to caking, of only dissolving very slowly in water, of being poor excipients for compression or of not satisfying the criteria of identification and of purity laid down in some pharmacopoeias.

The Applicant Company has thus sought to develop an anhydrous lactitol crystalline composition, of very high crystalline purity, which does not have the faults of flow, of caking, of dissolution or of compression exhibited by known lactitol powders. It might certainly have been thought that the need identified could be satisfied by other polyols. However, it is found that this is not the case because none of them simultaneously possesses all the metabolic and physicochemical characteristics exhibited by lactitol.

It is to the credit of the Applicant Company to have succeeded, against all expectations, after having carried out intense research into the subject, in preparing an anhydrous crystalline lactitol composition which does not exhibit the faults found in known lactitol powders while being high in crystalline purity. It has demonstrated, surprisingly and unexpectedly, that such a crystalline composition can be prepared under specific conditions from a solution or a suspension by a process related to atomization, which had never made it possible in the past directly to obtain products of high crystalline purity. It should be noted in this respect that this is all the more surprising since this atomization technique appeared, according to Patent Application JP 2-255 694, as being contraindicated in producing such a result.

The invention consequently relates, firstly, to an anhydrous crystalline lactitol composition which exhibits an essentially porous and cellular structure and a crystalline purity greater than or equal to 90%.

The first essential characteristic of the lactitol composition is due to the fact that it is crystallized essentially in the anhydrous form, this crystalline state conferring very high stability on it with respect to moisture. It consequently has a low tendency to set solid or to cake. It is thus easy to use.

According to a second essential characteristic, the anhydrous lactitol crystalline composition according to the invention exhibits a crystalline purity greater than or equal to 90%. The notion of crystalline purity must be understood, in the context of the present invention, as corresponding to the percentage of crystalline lactitol in the anhydrous form with a melting point of between 140° C. and 155° C., expressed as dry weight with respect to all the lactitol present in the crystalline composition. This crystalline purity can easily be evaluated by differential thermal analysis, a product which is completely crystallized in the anhydrous form with a melting point of between 145° C. and 155° C. being considered as exhibiting an enthalpy of melting of the order of 150 joules/g. This purity is then calculated by dividing, by 150 joules/g, the value of the enthalpy obtained in a sealed crucible for the anhydrous form with a melting point of between 145 and 155° C. present in the composition. The crystalline purity of the composition is preferably greater than or equal to 95% and better still greater than or equal to 98%.

The crystallinity of the composition in accordance with the invention is directly proportional to its enthalpy of melting, which, measured in a sealed crucible, is preferably greater than 135 J/g, more preferentially greater than 140 J/g and more preferentially still greater than 145 J/g.

It has been found, surprisingly and unexpectedly, that the composition in accordance with the invention has a crystallinity generally greater than or equal to that of an anhydrous lactitol with an equivalent lactitol content obtained by kneading-extrusion. The notion of lactitol content must be understood, in the context of the present invention, in its chemical sense, that is to say as corresponding to the percentage of lactitol, expressed as dry/dry weight, with respect to all the carbohydrates present in the composition on a dry basis. These carbohydrates can be sugars, such as lactose, or polyols, such as mannitol, sorbitol or lactulitol. This content is generally measured by high performance liquid chromatography.

Thus it is that the crystalline lactitol composition in accordance with the invention preferably has a lactitol content of at least 92%. However, it is preferable, in order for it to be able to crystallize directly and more completely, for it to exhibit a lactitol content greater than or equal to 95% and better still greater than or equal to 98%. The ideal is to achieve a content in the region of or greater than 99%.

Moreover, it is also preferable for the composition in accordance with the invention to contain only a small level of polyols chosen from sorbitol, mannitol and lactulitol. The level of these polyols is preferably less than 5% and better still less than 2%, with respect to the composition on a dry basis. This is because it has been found that their presence has a significant detrimental effect on the properties of the composition in accordance with the invention. This is not the case, or is to a much lesser extent, when the composition contains certain other substances. This explains why the crystalline lactitol composition can contain, without disadvantage, greater or lesser amounts of such substances, depending on the use to which it is dedicated.

Mention may be made, among substances capable of entering into the crystalline lactitol composition without posing a major problem, of, for example, powerful sweeteners, dyes, fragrances, flavours, vitamins, minerals, pharmaceutical or veterinary active principles, fatty acid esters, organic or inorganic acids and their salts, or proteinaceous materials, such as proteins, amino acids and enzymes.

According to a third essential characteristic, the crystalline lactitol composition in accordance with the invention exhibits an essentially porous and cellular structure. Under an optical microscope, it is found that it is essentially composed of spherical particles without sharp edges, which distinguishes it very clearly from lactitol powders obtained by crystallization from water or by kneading-extrusion. Under an electron microscope, it is found that the composition in accordance with the invention contains particles composed of microparticles agglomerated with one another. The composition according to the invention ordinarily exhibits, for this reason, a lower aerated density than those of known lactitol powders. This density can be measured, for example by using an apparatus sold by the company Hosokawa under the trademark "Poudre Tester", by applying the method recommended for measuring a bulk density. Under these conditions, for a particle size fraction of between 100 and 200 microns, the composition in accordance with the invention exhibits a bulk density of between approximately 100 and approximately 620 g/l, preferably 200 and 600 g/l and more preferentially between 300 and 550 g/l. Its bulk density is commonly between 350 and 500 g/l.

It should be noted that the essentially porous and cellular structure of the composition is clearly differentiated from the structure of a lactitol crystallized from water or of an extruded lactitol, which are in both cases composed of highly angular cubic or parallelepipedal particles.

BRIEF DESCRIPTION OF THE DRAWINGS

This structure is illustrated on the attached drawing, in which:

FIG. 1 to 3 represent photographs obtained by electron microscopy respectively for:

Figure 1:
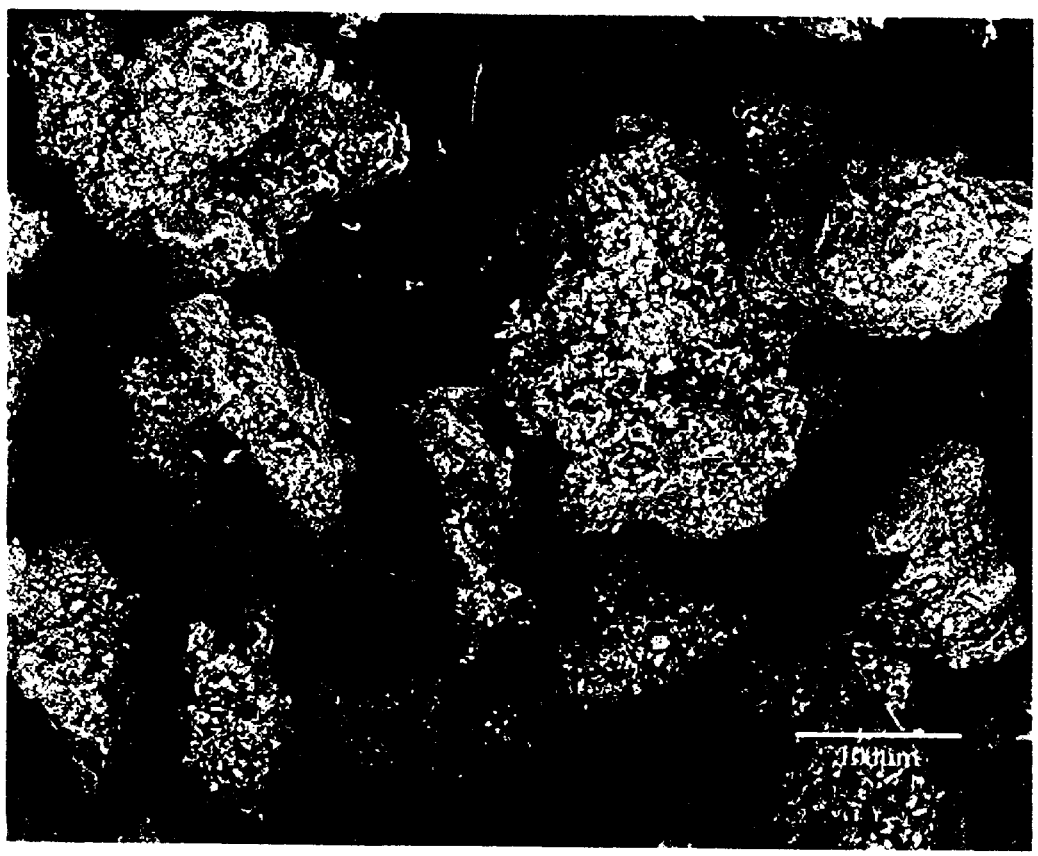

a lactitol composition according to the invention;

a lactitol powder sold by the Cultor Company under the name Lactitol AC; and a lactitol powder extruded according to the conditions given in JP 2-255694.

Thus it is that the crystalline lactitol composition in accordance with the invention is virtually devoid of particles exhibiting characteristics of shape and of appearance similar to those found in lactitol powders in which the lactitol has been crystallized from water or extruded.

The crystalline composition in accordance with the invention generally possesses a specific surface of between 0.2 m²/g and 0.45 m²/g for a particle size fraction of 50 to 200 microns. These specific surface values are greater than those obtained in the case of an anhydrous lactitol prepared by crystallization from water.

Moreover, the Applicant Company has found, by measuring the mercury porosity of particle size fractions of 100 to 200 microns that the composition in accordance with the invention is composed of particles possessing open pores with a size of between 1 and 10 microns.

The water level, determined by heating the crystalline lactitol composition in accordance with the invention in an oven at 130° C. for 2 hours, is preferably less than 2% and more preferentially still less than 1%. Generally, this level is even less than 0.5%, indeed 0.3%.

As regards the functional characteristics of the crystalline lactitol composition in accordance with the invention, the Applicant Company has evaluated its ability to flow by using the apparatus sold by the company Hosokawa. This apparatus makes it possible to measure, under standardized and reproducible conditions, the ability to flow of a powder and to calculate a flow grade also known as the Carr index. The composition in accordance with the invention exhibits an excellent flow grade, of between 75 and 90. This value is preferably between 77 and 90 and more preferentially between 80 and 90.

Moreover, the ability to flow of the composition which forms the subject of the invention is ordinarily greater than those of lactitol powders obtained by crystallization from water.

It may be thought that the excellent ability to flow of the composition in accordance with the invention is explained by the combination of several of its physicochemical characteristics, namely, in particular, the absence of significant electrostatic charges at the surface of its constituent particles, its high crystalline purity with respect to anhydrous lactitol, its lactitol content and finally the characteristic shape of its constituent particles. This excellent ability to flow is advantageous because it makes it very easy to fill and to empty hoppers, receptacles or other containers, such as sachets or hard gelatin capsules, for example.

A second essential functional property of the crystalline lactitol composition in accordance with the invention is its ability to dissolve very quickly in water. To measure this rate of dissolution, a test A is carried out, which test consists in introducing, into 150 grams of demineralized and degassed water maintained at 20° C. and stirred by a magnetic bar at 200 r/minute in a 250 ml low form beaker, exactly 5 grams of a 100 to 200 micron particle size fraction of the product to be tested. The dissolution time corresponds to the time necessary, after introduction of the particle size fraction, to obtain perfect visual clarity of the preparation. Under these conditions, the composition in accordance with the invention generally possesses a rate of dissolution of less than 20 seconds. The preferred composition dissolves in less than 15 seconds while the ideal composition only requires a time of less than 12 seconds. These times are generally lower than those obtained with all the lactitol powders currently available commercially. It is understood that this property of rapid dissolution is an undeniable advantage, for example in the manufacture of foodstuffs or pharmaceutical products to be dissolved before they are ingested.

The crystalline lactitol composition in accordance with the invention also possesses other advantageous characteristics. Mention may be made of its very good ability to be compressed, in preparing tablets to be chewed or sucked, and of its very good ability to be mixed with other products.

The invention relates, secondly, to a process for the preparation of an anhydrous lactitol crystalline composition exhibiting an essentially porous and cellular structure and a crystalline purity greater than or equal to 90%.

The crystalline lactitol composition in accordance with the invention is capable of being obtained by spraying a syrup with a relatively high lactitol content, with respect to the amount of carbohydrates present in this syrup, over a moving pulverulent bed of crystalline lactitol particles with a content at least equal to that of the syrup. It has been found that the lactitol content of the syrup must preferably be greater than or equal to 92% in order for it to be possible to crystallize the lactitol in a sufficiently short period of time and to a sufficient extent.

This lactitol syrup is generally a completely clear lactitol solution. It can also be a suspension which is slightly opaque because of the presence within the syrup of lactitol crystals. In this case, it is preferable for these crystals to be very small in size.

The crystalline lactitol composition can in particular be obtained by making use of the process comprising the following stages:

preparation of a lactitol syrup having a solids content of at least 50% and preferably exhibiting a lactitol content greater than or equal to 92%, fine spraying this syrup onto a moving pulverulent bed of crystalline lactitol particles with a lactitol content preferably at least equal to that of the syrup; the mass of the bed constantly representing at least twice the mass of the sprayed syrup, drying the pulverulent bed and the syrup in order to obtain crystallization of the lactitol in the anhydrous form with a melting point of between 145 and 155° C., optional maturation of the crystalline lactitol composition until it exhibits a sufficient crystallinity and preferably an enthalpy of melting greater than or equal to 135 J/g, optional recycling of the crystalline lactitol composition after maturation in order for it to constitute a new pulverulent bed of crystalline lactitol.

In contrast to what might have been thought, this technique makes it possible to obtain a composition containing lactitol crystallized up to at least 90% in the anhydrous form with a melting point of between 145 and 155° C., without necessarily using for this a moving bed of particles of lactitol crystallized in this anhydrous state.

The properties of the composition in accordance with the invention can be adjusted by modifying the lactitol content of the syrup, the solids content of the syrup, the fineness of the spraying, the shape of the crystalline lactitol particles constituting the pulverulent bed, the means whereby these particles are moved, the temperature of the bed, the drying temperature and the respective masses of the bed and of sprayed syrup.

As regards the lactitol content of the syrup, it is preferable, without this being essential, for it to be greater than or equal to 95%, better still greater than or equal to 98%, the ideal being to choose a content in the region of or greater than 99%.

The lactitol syrup preferably exhibits a solids content of between 55 and 99.5%. In general, this solids content is advantageously between 60 and 90% and better between 65 and 85%.

It is preferable to avoid coarse spraying of the syrup, in which case adhesion, poor crystallization of the lactitol and a very large increase in the density are observed, which is not desired. Consequently, in order for the crystalline lactitol composition to exhibit the specific properties described above, it is advisable to use equipment which makes it possible to form very fine droplets, indeed a mist, from the syrup.

As regards the nature of the lactitol particles constituting the pulverulent bed, it is preferable for them also to exhibit a high lactitol content, always at least equal to that of the syrup employed. In order to obtain a good result, it is also preferable for this bed also to be fairly low in density, that is to say to exhibit a density of less than 620 g/l and better still less than 600 g/l. The ideal is to use for this bed lactitol particles exhibiting all the characteristics of the crystalline lactitol composition in accordance with the invention. This can be obtained by carrying out a partial recycling of the composition in accordance with the invention, which then acts as pulverulent bed of crystalline lactitol. It is highly advantageous to proceed in this way but it is then preferable to mill or to sieve the composition in accordance with the invention in order to use only particles with a size of less than 150 microns and better still with a size of less than 90 microns.

The particles constituting the pulverulent bed can be moved mechanically or by blowing air. The latter possibility is preferred because it is easy, by choosing the temperature of the air, to adjust the temperature of the bed to a value of between 60 and 110° C. and, by regulating the air flow rates, to adjust the properties of the crystalline lactitol composition.

It is generally preferable for the temperature of this bed to be maintained between 65 and 105° C.; the ideal being between 70 and 90° C. It is also preferable for the mass of the pulverulent bed constantly to represent three times or better five times the mass of sprayed syrup. When a partial recycling of the composition according to the invention is carried out, in order for it to act as pulverulent bed, it is sufficient to adjust the input flow rate of syrup in order for it only to represent at most 25%, or better at most 17%, of the input flow rate of recycled composition.

The pulverulent bed over which the syrup has been sprayed must be dried so as to obtain a final water level not exceeding 2%, preferably 1% and more preferentially 0.5% of the composition.

The Applicant Company has demonstrated that the crystalline lactitol composition can advantageously be manufactured continuously, for example by using an atomization tower of M.S.D. type from the company Niro-Atomizer which makes it possible, by virtue of its design, to reproduce all the essential stages of the process in accordance with the invention.

This is because this equipment makes it possible, using the nozzle which it contains, very finely to spray a syrup having a temperature of between 45 and 75° C. and a solids content of between 55 and 80% over a bed of lactitol particles which has been brought into motion and maintained in motion with air. Moreover, this equipment makes it possible simultaneously to dry using air exiting from the tower. An air inlet temperature of between 160 and 280° C. and flow rates for materials entering can advantageously be chosen such that the temperature of the air exiting from the tower is between 60 and 130° C. and better still between 80 and 100° C. This equipment also makes it possible to carry out an optional partial recycling of the crystalline lactitol composition and to disperse it very finely in the top of the tower, around the nozzle for spraying the syrup.

The crystalline lactitol composition obtained according to the process in accordance with the invention can, if necessary, subsequently be granulated, so as to modify its particle size distribution. This granulation can be carried out with water, with steam or using a syrup preferably containing lactitol.

The crystalline lactitol composition in accordance with the invention can advantageously be employed as sweetening agent, bulking or texturizing agent, excipient or vehicle for various additives. It is particularly recommended, because of its specific properties, in the manufacture of soluble tablets and powders in the food and pharmaceutical fields or other fields. However, nothing prevents it from being used for any other purpose, such as, for example, to formulate chewing gum or confectionery.

The invention will be still better understood using the following example, which is not to be considered as limiting and only reports certain embodiments and certain advantageous properties of the crystalline lactitol composition according to the invention.

EXAMPLE

Preparation of Crystalline Lactitol Compositions According to the Invention and Comparison with the Products of the Prior Art A lactitol solution with a solids content of 85% is prepared by dissolving lactitol monohydrate crystals exhibiting a lactitol content of 99.0%. This solution is brought to 100° C. and then maintained at this temperature.

This solution is sprayed, using a nozzle, over 100 g of a finely milled lactitol powder brought into motion in an apparatus of Aeromatic type, the lactitol having been crystallized from water in monohydrate form. The Lacty® M crystalline powder sold by the company C.C.A. is used for this. This powder acts as pulverulent bed of crystalline lactitol. This powder is brought into motion by fluidization with air at 80° C.

The fine spraying of the syrup over the moving pulverulent bed of particles is continued at a constant flow rate, so hat, after half an hour, the amount of material in the apparatus is 900 g. The spraying is halted and the product obtained is dried for 15 minutes by maintaining it in motion by fluidization with air at 80° C. It is then slowly cooled in order to cause it to mature.

The experiment described above is repeated, using the matured product obtained above as starting pulverulent bed.

Under these conditions, it is found that the final lactitol composition obtained following the second experiment is virtually devoid of particles exhibiting characteristics of shape and of appearance similar to those found in the starting Lacty® M lactitol monohydrate powder. Indeed, the composition is essentially porous and cellular and is composed of essentially spherical anhydrous particles devoid of sharp edges and composed of a multitude of crystalline microparticles agglomerated with one another. This composition in accordance with the invention is known as I. Its main characteristics are given in the table below.

|  | Composition according to the invention I | Compositions of the prior art | |
| --- | --- | --- | --- |
|  |  | Crystallized from water | Extruded |
| Lactitol content | 99.0% | 99.8% | 99.0% |
| Water level (Karl Fischer) | 0.4% | 0.25% | 0.4% |
| Enthalpy of melting (±2 J/g) of the 145–155° C. crystalline form | 148 J/g | 148.45 J/g | 140.0 J/g |
| Melting temperature at the peak (±0.5° C.) | 150.9° C. | 150° C. | 149.4° C. |
| Structure | Porous and cellular Agglomerated microcrystals | Very dense, non-porous | Dense and non-porous |
| Density (g/l) | 446 | 685 | 628 |
| Carr flow index | 79 | 77 | 75 |
| Rate of dissolution (Test A) | 11 | 14 | 12 |

The composition I in accordance with the invention is compared with various lactitol powders of the prior art, that is to say:

a crystalline powder containing anhydrous lactitol crystals, which are obtained by crystallization from water, sold by the company Cultor under the name Lactitol AC;

and a lactitol powder extruded according to the conditions given in Patent Application JP 2-255 694.

The structure of the various products is observed under an optical microscope in polarized light and under an electron microscope, on particle size fractions of 100 to 200 microns. It is found, under an optical microscope, that, in comparison with the powder crystallized from water and with the extruded powder, the composition I according to the invention is essentially composed of spherical particles without sharp edges, which distinguishes it very clearly from the other two crystalline powders.

Figure 2:
Figure 3:
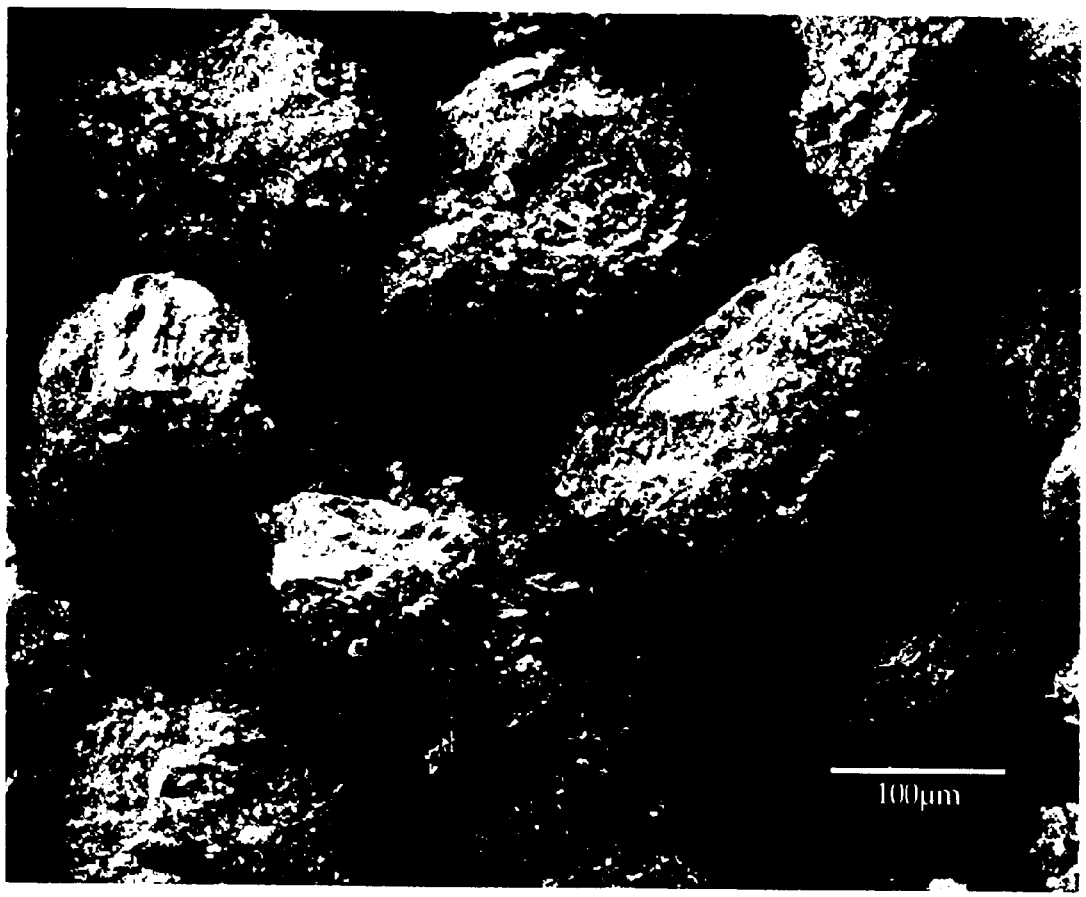

On comparing the photographs obtained by electron microscopy for the composition I (FIG. 1), the powder crystallized from water (FIG. 2) and the extruded powder (FIG. 3), it is found that the crystalline lactitol composition according to the invention is the only one to possess essentially a porous and cellular structure and contains particles composed of crystalline microparticles which are agglomerated with one another. The density of these particles appears clearly lower than that of the particles of the products of the prior art. This is because the latter exhibit a dense and compact structure, with smooth particle surfaces and sharp edges which are very different from those found for the composition according to the invention.

A number of functional characteristics of the compositions according to the invention are given in the following table. In contrast to the compositions of the prior art, the compositions in accordance with the invention advantageously combine properties until now not found simultaneously. This is because they simultaneously possess the characteristics of being compressible, of easily flowing and of dissolving very rapidly in water.

Moreover, it appears that they are very weakly hygroscopic, which is an undeniable advantage in their storage and their use.

I claim:

1. An anhydrous crystalline composition having porous and cellular structure consisting of anhydrous and crystalline lactitol having a crystalline purity of greater than or equal to 90%.

2. The composition according to claim 1, having a crystalline purity greater than or equal to 92%.

3. The composition according to claim 2, having a crystalline purity greater than or equal to 95%.

4. The composition according to claim 3, having a crystalline purity greater than or equal to 98%.

5. The composition according to claim 4, having a crystalline purity greater than or equal to 99%.

6. The composition according to claim 1, having an enthalpy of melting greater than 135 J/g.

7. The composition according to claim 6, having an enthalpy of melting greater than 140 J/g.

8. The composition according to claim 7, having an enthalpy of melting greater than 145 J/g.

9. The composition according to claim 6, having a crystalline purity greater than or equal to 95%.

10. The composition according to claim 9, having a crystalline purity greater than or equal to 98%.

11. The composition according to claim 1, comprising, by weight on a dry basis, less than 5% of polyols chosen from sorbitol, mannitol and lactulitol.

12. The composition according to claim 11, comprising, by weight on a dry basis, less than 2% of polyols chosen from sorbitol, mannitol and lactulitol.

13. The composition according to claim 1, having a bulk density of between 100 and 620 g/l.

14. The composition according to claim 13, having a bulk density of between 200 and 600 g/l.

15. The composition according to claim 14, having a bulk density of between 300 and 550 g/l.

16. The composition according to claim 1, having a Carr flow index value of between 75 and 90.

17. The composition according to claim 16, having a Carr flow index value of between 77 and 90.

18. The composition according to claim 17, having a Carr flow index value of between 80 and 90.

19. The composition according to claim 1, having a water level of less than 2%.

20. The composition according to claim 19, having a water level of less than 1%.

21. The composition according to claim 20, having a water level of less than 0.5%.

22. A pharmaceutical or food composition comprising the lactitol composition of claim 1 and one or more additives chosen from intense sweeteners, dyes, fragrances, flavors, vitamins, minerals, pharmaceutical active principles, fatty esters of fatty acids, organic and inorganic acids and their salts.

23. The composition according to claim 1, having a rate of dissolution in water according to a test A of less than 20 seconds.

24. The composition according to claim 23, having a rate of dissolution in water according to a test A of less than 15 seconds.

25. The composition according to claim 24, having a rate of dissolution in water according to a test A of less than 12 seconds.

26. A process for producing a crystalline composition of claim 1, comprising the following steps:

preparation of a lactitol syrup having a solids content of at least 50% and;

fine spraying this syrup onto a moving pulverulent bed of crystalline lactitol particles with a purity at least equal to that of the syrup; the mass of the bed constantly representing at least twice the mass of the sprayed syrup;

drying the pulverulent bed and the syrup in order to obtain crystallization of the lactitol in the anhydrous form with a melting point of between 145 and 155° C.;

optional maturation of the crystalline lactitol composition until it exhibits a sufficient crystallinity;

optional recycling of the crystalline lactitol composition after maturation in order for it to constitute a new pulverulent bed of crystalline lactitol.

27. The process according to claim 26, wherein the maturation of the crystalline lactitol composition is carried on until it exhibits and enthalpy of melting greater or equal to 135 J/g.

* * * * *